United States Patent
Kennedy, III

(10) Patent No.: US 11,484,027 B2
(45) Date of Patent: Nov. 1, 2022

(54) AIR FILTER WITH PATHOGEN MONITORING AND INACTIVATION

(71) Applicant: Industrial Polymers and Chemicals, Inc., Shrewsbury, MA (US)

(72) Inventor: Thomas J. Kennedy, III, Wilbraham, MA (US)

(73) Assignee: Industrial Polymers and Chemicals, Inc., Shrewsbury, MA (US)

( * ) Notice: Subject to any disclaimer, the term of this patent is extended or adjusted under 35 U.S.C. 154(b) by 0 days.

(21) Appl. No.: 17/507,344

(22) Filed: Oct. 21, 2021

(65) Prior Publication Data

US 2022/0132838 A1    May 5, 2022

Related U.S. Application Data

(60) Provisional application No. 63/252,514, filed on Oct. 5, 2021, provisional application No. 63/107,388, filed on Oct. 29, 2020.

(51) Int. Cl.
*A01N 33/12* (2006.01)
*A61L 9/01* (2006.01)
(Continued)

(52) U.S. Cl.
CPC ............ *A01N 25/10* (2013.01); *A01N 33/12* (2013.01); *A61L 9/01* (2013.01); *A61L 2101/32* (2020.08);
(Continued)

(58) Field of Classification Search
CPC .......... A01N 25/10; A01N 33/12; A61L 9/01; A61L 2101/32; A61L 2209/14; A61L 2209/16
See application file for complete search history.

(56) References Cited

U.S. PATENT DOCUMENTS 5,787,885 A     8/1998  Lemelson
5,976,462 A *  11/1999  Stone .................. A01N 25/24
                                                    424/404
(Continued)

FOREIGN PATENT DOCUMENTS

AU    2013211460 B2   11/2014
AU    2015200865 A1    3/2015
(Continued)

OTHER PUBLICATIONS

Air Sampling Tools for Detection of SARS-CoV-2 in Droplets & Aerosols.
(Continued)

*Primary Examiner* — Sean E Conley
*Assistant Examiner* — Brendan A Hensel
(74) *Attorney, Agent, or Firm* — Goodwin Procter LLP

(57) ABSTRACT

An improved technology for inactivation of viruses, for example the SARS-CoV-2 virus that is causing the Covid-19 pandemic, is described. The technology can include a device that includes a substrate coated in a polymer that is infused with a pathogen inactivating material. In various embodiments, at a given time, a portion of the pathogen inactivating material is exposed to the environment, and the device is configured to periodically or intermittently expose additional pathogen inactivating material to the environment. For example, the polymer can be ablative or sacrificial.

18 Claims, 4 Drawing Sheets

(51) Int. Cl.
*A61L 101/32* (2006.01)
*A01N 25/10* (2006.01)

(52) U.S. Cl.
CPC ....... *A61L 2209/14* (2013.01); *A61L 2209/16* (2013.01)

(56) References Cited

U.S. PATENT DOCUMENTS

| | | | |
|---|---|---|---|
| 6,834,533 B2 | 12/2004 | Megerle | |
| 7,311,752 B2 | 12/2007 | Tepper et al. | |
| 7,579,077 B2 | 8/2009 | Dubrow et al. | |
| 7,767,150 B1 | 8/2010 | Zaromb et al. | |
| 8,030,025 B2 | 10/2011 | Boone et al. | |
| 8,168,120 B1 | 5/2012 | Younis | |
| 8,323,213 B2 | 12/2012 | Kim | |
| 8,551,408 B2 | 10/2013 | Beaudet et al. | |
| 8,715,503 B2 | 5/2014 | Jones et al. | |
| 8,734,718 B2 | 5/2014 | Pacey, Jr. et al. | |
| 8,784,660 B2 | 7/2014 | Jones et al. | |
| 9,452,209 B2 | 9/2016 | Ballou et al. | |
| 9,501,049 B2 | 11/2016 | Balakrishnan et al. | |
| 10,345,216 B2 | 7/2019 | Clayton et al. | |
| 10,794,603 B2 | 10/2020 | Rosen et al. | |
| 2002/0165260 A1* | 11/2002 | Dyer | A61K 31/14 514/642 |
| 2002/0165594 A1* | 11/2002 | Biel | A61K 41/0057 607/89 |
| 2005/0038498 A1 | 2/2005 | Dubrow et al. | |
| 2006/0223838 A1 | 10/2006 | Jiang et al. | |
| 2007/0042348 A1 | 2/2007 | Amano et al. | |
| 2009/0259138 A1 | 10/2009 | Lin et al. | |
| 2009/0307787 A1 | 12/2009 | Grosveld et al. | |
| 2010/0285972 A1 | 11/2010 | Dubrow et al. | |
| 2013/0018112 A1 | 1/2013 | Thielemans et al. | |
| 2017/0027168 A1 | 2/2017 | Heath | |
| 2017/0124276 A1 | 5/2017 | Tee | |
| 2018/0009995 A1* | 1/2018 | Kaufold | C08L 3/08 |
| 2019/0211294 A1 | 7/2019 | Karnieli | |
| 2019/0360686 A1 | 11/2019 | Pendo et al. | |
| 2020/0229411 A1 | 7/2020 | Leo | |
| 2020/0393159 A1 | 12/2020 | Takayanagi | |
| 2021/0015108 A1* | 1/2021 | McDaniel | A01N 63/40 |
| 2021/0154619 A1 | 5/2021 | Maggio | |

FOREIGN PATENT DOCUMENTS

| | | |
|---|---|---|
| CN | 105222244 A | 1/2016 |
| CN | 205079352 U | 3/2016 |
| CN | 206131408 U | 4/2017 |
| CN | 107763736 A | 3/2018 |
| CN | 207540021 U | 6/2018 |
| CN | 109268970 A | 1/2019 |
| CN | 111237690 A | 6/2020 |
| CN | 210861567 U | 6/2020 |
| CN | 111380154 A | 7/2020 |
| CN | 111594917 A | 8/2020 |
| CN | 111637589 A | 9/2020 |
| CN | 111674229 A | 9/2020 |
| CN | 112138482 A | 12/2020 |
| CN | 212457162 U | 2/2021 |
| CN | 112696781 A | 4/2021 |
| CN | 213269512 U | 5/2021 |
| DE | 102014215735 A1 | 2/2016 |
| EP | 1027431 A2 | 8/2000 |
| EP | 1318195 A1 | 6/2003 |
| EP | 1601948 A2 | 12/2005 |
| EP | 3495811 A1 | 6/2019 |
| JP | 2011021931 A | 2/2011 |
| JP | 5889136 B2 | 3/2016 |
| KR | 100585223 B1 | 6/2006 |
| KR | 101075511 B1 | 10/2011 |
| KR | 101348750 B1 | 1/2014 |
| KR | 102219356 B1 | 2/2021 |
| WO | WO-201293799 A2 | 7/2012 |
| WO | WO-2018074052 A1 | 4/2018 |
| WO | WO-2021107391 A1 | 6/2021 |

OTHER PUBLICATIONS

Meixuan Li, et al. "Challenges and Perspectives for Biosensing of Bioaerosol Containing Pathogenic Microorganisms", Micromachines 2021, 12(7), 798; https://doi.org/10.3390/mi12070798.
Indoor Air Quality Monitoring (https://www.senseware.co/airborne-monitoring/).

* cited by examiner

| Standard 52.2 Minimum Efficiency Reporting Value (MERV) | Composite Average Particle Size Efficiency, % in Size Range, μm | | | Average Arrestance, % |
|---|---|---|---|---|
| | Range 1 (0.3-1.0) | Range 2 (1.0-3.0) | Range 3 (3.0-10.0) | |
| 1 | n/a | n/a | E3 < 20 | $A_{avg}$ < 65 |
| 2 | n/a | n/a | E3 < 20 | 65 ≤ $A_{avg}$ < 70 |
| 3 | n/a | n/a | E3 < 20 | 70 ≤ $A_{avg}$ < 75 |
| 4 | n/a | n/a | E3 < 20 | 75 ≤ $A_{avg}$ |
| 5 | n/a | n/a | 20 ≤ E3 | n/a |
| 6 | n/a | n/a | 35 ≤ E3 | n/a |
| 7 | n/a | n/a | 50 ≤ E3 | n/a |
| 8 | n/a | 20 ≤ $E_2$ | 70 ≤ E3 | n/a |
| 9 | n/a | 35 ≤ $E_2$ | 75 ≤ E3 | n/a |
| 10 | n/a | 50 ≤ $E_2$ | 80 ≤ E3 | n/a |
| 11 | 20 ≤ $E_1$ | 65 ≤ $E_2$ | 85 ≤ E3 | n/a |
| 12 | 35 ≤ $E_1$ | 80 ≤ $E_2$ | 90 ≤ E3 | n/a |
| 13 | 50 ≤ $E_1$ | 85 ≤ $E_2$ | 90 ≤ E3 | n/a |
| 14 | 75 ≤ $E_1$ | 90 ≤ $E_2$ | 95 ≤ E3 | n/a |
| 15 | 85 ≤ $E_1$ | 90 ≤ $E_2$ | 95 ≤ E3 | n/a |
| 16 | 95 ≤ $E_1$ | 95 ≤ $E_2$ | 95 ≤ E3 | n/a |

FIG. 6

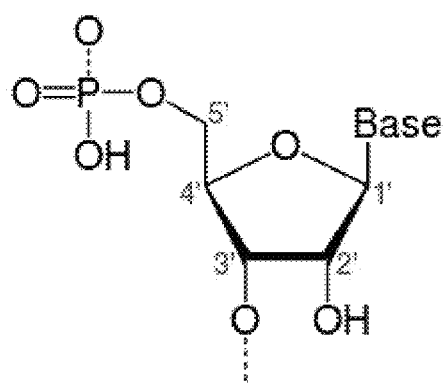

FIG. 7

AIR FILTER WITH PATHOGEN MONITORING AND INACTIVATION

CROSS-REFERENCE TO RELATED APPLICATIONS

This application claims the benefit of priority to U.S. Provisional Patent Application No. 63/107,388 entitled "Air Filter with Pathogen Monitoring and Inactivation," filed on Oct. 29, 2020 and U.S. Provisional Patent Application No. 63/252,514 entitled "Air Filter with Pathogen Monitoring and Inactivation," filed on Oct. 5, 2021, the contents of both of which are incorporated by reference herein in their entirety.

TECHNICAL FIELD

The present invention generally relates to pathogen inactivating agents and, more particularly, to pathogen inactivating agents infused within a polymer in a manner such that additional pathogen inactivating material is periodically or intermittently exposed to the environment.

BACKGROUND

Air filters for HVAC systems provide excellent filtration of particles. Depending upon the rating of the filter, smaller and smaller particles may be filtered out of the air. A specific type of filter, high efficiency particulate air (HEPA) filter, is utilized to filter micron and submicron particles from the air.

While very fine particle filters offer trapping of allergens and other problem materials such as fine dust, all of these passive air filters do not allow for the inactivation of pathogens that may be borne by the air as it flows through the HVAC system. HEPA filters may also cause a high pressure drop across the filter, resulting in poor airflow through the HVAC system.

Thus, there is therefore a need for a long-lasting, pathogen inactivating, and high percentage capture air filter for HVAC systems.

SUMMARY

The embodiment is the use of air filter or filters comprised of paper, woven fiberglass, nonwoven fiberglass, nonwoven polymers, and the like where the air filter or filters further comprise a method of inactivating pathogens through the use of a compound or compounds that are infused or coated into or onto the air filters.

The air filter or filters further comprise a polymer that is infused or mixed with a compound, such as a biocide or virucide, that will inactivate pathogens such as viruses and bacteria. The polymer may also have ablative or sacrificial characteristics where the surface of the polymer may wear down with time, exposing a new fresh surface of the polymer.

The ablative or sacrificial polymer may be an emulsion polymer comprised of a polyvinyl acetate and acrylate backbone where the outer surface of the polymer will be worn away over time, exposing a new surface to the environment.

The sacrificial polymer may also be from the group of poly lactic acid (PLA), polycaprolactone (PCL), poly(lactic-co-glycolic acid) (PLGA), polyglycidyl methacrylate (PGMA), gelatin, polysaccharides, cellulose acetate, methyl cellulose, ethyl cellulose, hydroxyethyl cellulose, and polyvinyl acetate copolymers. These polymers will degrade readily in standard temperature and pressure (STP) conditions such as the environment of an office building, school, or residence. In the case of a residence, the residence may be temporary, such as a hotel or motel, or permanent, such as a house or apartment.

The virucide or biocide infused polymer may also be compounded such that, when coated onto the filter substrate, provides a continuous supply of the virucide or virucide to the air that is flowing through the filter. One method of accomplishing this is to introduce a large excess of virucide or biocide into the polymer mixture such that the virucide or biocide comes to the surface of the polymer through surface energy, diffusion, capillary action, or other passive transport mechanisms.

The polymer that is coated on the filter system may also be of such a nature that it is incompatible with the biocide or virucide such that the biocide or virucide, or any other material that would inactivate a pathogen, is allowed to ooze or flow out of the polymer matrix. This would be similar to a permanently oiled bearing where oil is infused into a sintered bearing and thus has long life lubrication as the oil oozes out of the sintered bearing. The polymer matrix may be a solid, solution, or emulsion type. The polymer may be borne by an organic solvent or may be waterborne or maybe 100% solids.

The virucide or biocide may be a blend of virucides or biocides, each having a different target area of pathogens.

Filter papers are used in many types of applications including air filters for HVAC units and automobiles, coffee filters, fuel filters, chromatography separation, laboratory filters, and teabags to name a few applications. Porous air filters in HVAC systems may be manufactured in a manner to allow particles of different sizes to be trapped while other sizes may pass through the filter.

These filter papers have benefited from continued refinement and engineering to provide sustained and precise filtration methods for various materials.

Single-digit and fractional micron filtration is possible with many different types of filter paper. The filter papers may also be treated with biocides and virucides to improve the protection from infectious particles that may be circulating in the air.

The coating of the filter substrate may be accomplished by a spray, dip, roll, print, or other transfer process whereby an ablative or sacrificial polymer is transferred to the surface of the specialty paper. The ablative or sacrificial polymer may contain pathogen inactivating material such as a biocide or virucide. The roll process may be a Mayer rod process or a gravure process.

A fiberglass base material may be utilized for the HVAC filter. Here, the ablative or sacrificial polymer with a biocide or a virucide, or any other material that would inactivate a pathogen, is transferred to the fiberglass substrate. The fiberglass substrate may be woven or nonwoven. The ablative or sacrificial polymer will wear over time and exposed a new surface to the environment while it is coated on the fiberglass substrate.

The rating of the air filter may be of various levels. The American Society of Heating, Refrigerating and Air-Conditioning Engineers (ASHRAE) utilizes the standard as prescribed by ANSI/ASHRAE 52.2 for the Minimum Efficiency Reporting Value (MERV). A standard of MERV 13 or higher has been prescribed by the Center for Disease Control (CDC).

There are various biocides and virucides available in the marketplace for the inactivation of pathogens, including the SARS-CoV-2 virus that is causing the Covid-19 pandemic.

The biocides and virucides include materials that incorporate chlorinated molecules such as quaternary ammonium salts with a chlorine molecule attached. Benzalkonium chloride is an example of the material with a quaternary ammonium component and a chlorine component. Many other types of biocides and virucides are available such as sodium hypochlorite (commonly known as bleach), hydrogen peroxide, and isopropyl alcohol. Other molecules include boron, iodine, and other chlorine containing molecules.

BRIEF DESCRIPTION OF THE DRAWINGS

In the drawings, like reference characters generally refer to the same parts throughout the different views. In the following description, various embodiments of the present invention are described with reference to the following drawings, in which:

FIG. 6 is a table showing the MERV levels for air filters; and

FIG. 7 is a depiction of a furanose molecule with a phosphodiester bond.

DETAILED DESCRIPTION

Various embodiments described herein disclose a HVAC filters system that is coated with a polymer where the polymer contains an agent for inactivating viruses. Specifically, in some examples, the virucide in the polymer is used to inactivate the SARS-CoV-2 virus causing the Covid-19 pandemic.

The polymer may be an ablative or sacrificial polymer that will wear away at the surface over time, thus exposing new material to the environment. The polymer may also be a material that's incompatible with the inactivating agent such that the inactivating agent, a biocide or virucide for example, will ooze out of the polymer for a long period of time and thus inactivate viral particles when they impinge on the filter coated with this polymeric configuration.

An ablative or sacrificial polymer may also be known as a sacrificial material with the polymer subject to wear from environmental conditions. The ablation of a polymeric matrix may occur from thermal interaction, UV interaction, and other energetic, oxidating, or hydrogenating environmental interactions. The ablative or sacrificial polymer may also be comprised of nano composites. The sacrificial polymer may wear away and break down from environmental interactions.

The polymeric material, blended with a virucide or biocide, or any pathogen inactivating material, may be applied to the substrate by various means such as spraying, dipping, roll coating, and printing. Once the polymer is applied to the substrate, it may be cured or dried through various processes such as UV cure, drying in a heated oven, or air dried.

Test procedures, such as ISO-18184:2019, may be utilized to demonstrate the anti-viral capacity of a porous substrates. In accordance with ISO-18184:2019, samples of a non-woven fiberglass with an MERV rating of 13 treated with a polyvinyl acetate/acrylate copolymer infused with Stepan BTC-885, a benzalkonium chloride containing mixture, were tested. The pathogen that was tested utilizing the ISO-18184:2019 standard was the SARS-CoV-2 virus, WA1 strain. The results of the testing show that the polymer and virucide infused non-woven fiberglass MERV 13 filter inactivated all of the SARS-CoV-2 WA1 virus in 15 minutes. The test results are listed below in Table 1.

TABLE 1

| Protocol # | Project No. | Lot No. | Dilution | Test Virus | Contact time | $Log_{10}$ Reduction |
|---|---|---|---|---|---|---|
| IPAC.V.21.001 | 1123-101 | Test Material | N/A | Severe Acute Respirator Syndrome-Related Coronavirus 2 (SARS-CoV-2) (COVID-19 Virus) | 15 Minutes | ≥3.39 |

The substrate that the polymer is coated onto may be composed of various materials. The materials include both woven and nonwoven fiberglass, paper, nonwoven polymeric matrices, woven polymeric matrices, and similar support materials.

The polymeric coated substrate may then be fitted into a frame such that it may easily be inserted into an HVAC system that currently accepts regular types of filtration media.

Figure 1:
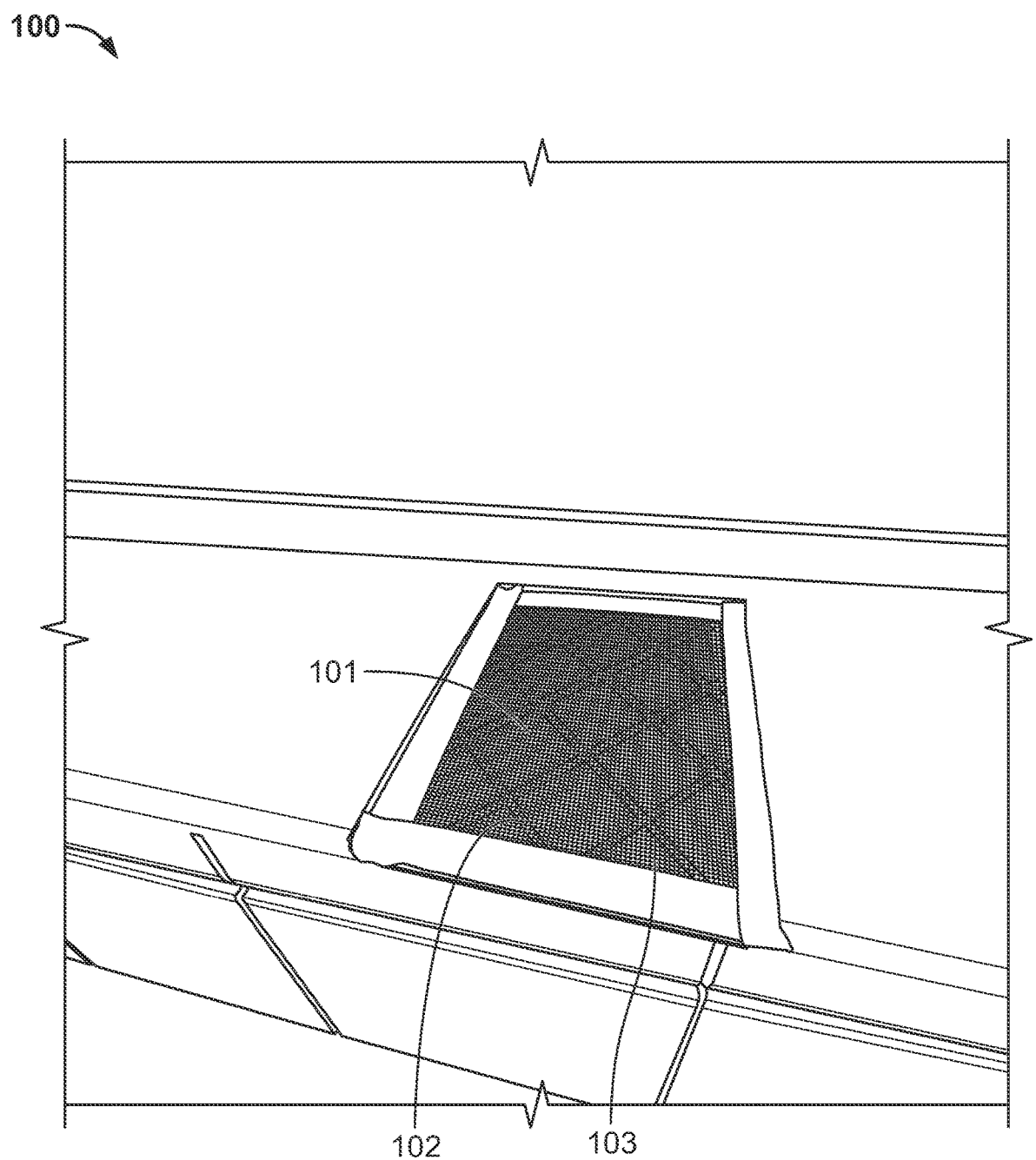
FIG. 1 illustrates an exemplary embodiment of an HVAC filter with a virucide infused coated fiberglass component.

FIG. 1 illustrates a type of HVAC filter 100 where a coated fiberglass mesh 101 has been incorporated into a paper frame. The fiberglass mesh is coated with an ablative or sacrificial polymer 102 composed of a polyvinyl acetate and poly acrylate copolymer. The ablative or sacrificial polymer also contains a virucide, benzalkonium chloride 103.

Figure 2:
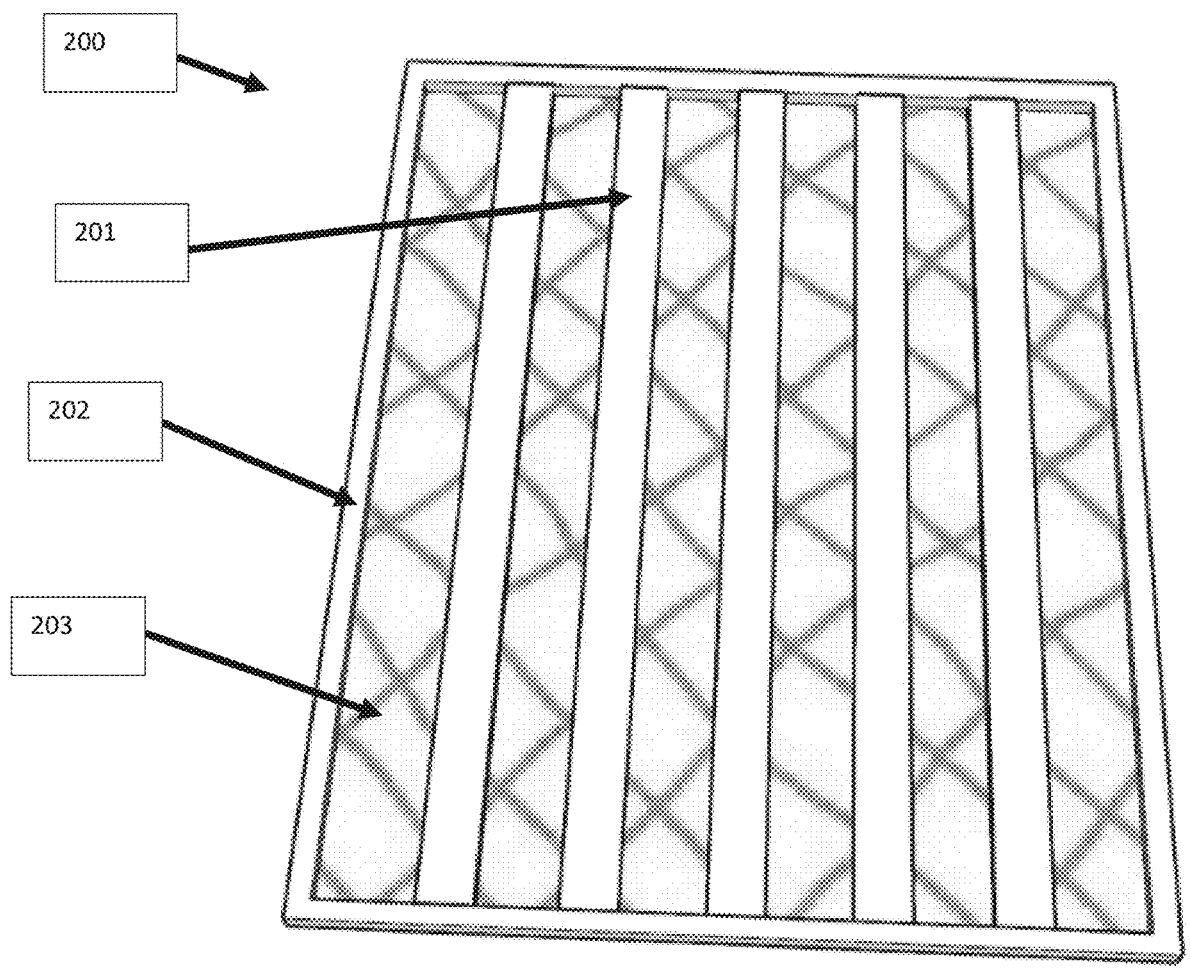
FIG. 2 is a rendering of a HVAC filter with a virucide infused substrate and a holder for the substrate.

FIG. 2 is a depiction of an air filter 200. The cross members 201 of the air filter frame 202 retain the filtration substrate 203. The filtration substrate 203 may be a woven or non-woven substrate. The material of the filter substrate 203 may be paper, fiberglass, or another suitable material. The filtration substrate 203 may be coated with a polymer where the polymer is infused with a virucide.

Figure 3:
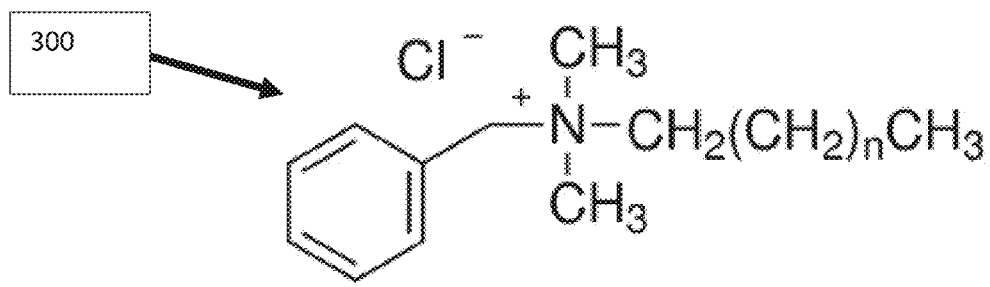
FIG. 3 is a chemical formula for benzalkonium chloride.

FIG. 3 depicts the benzalkonium chloride molecule 300, a strong anti-viral material.

Figure 4:
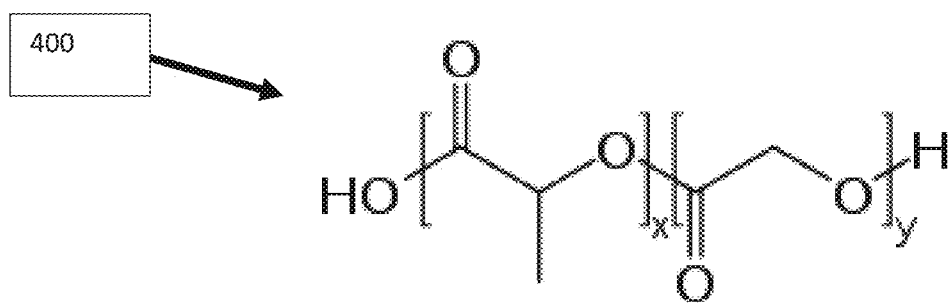
FIG. 4 is a chemical formula for poly(lactic-co-glycolic acid) (PLGA)

FIG. 4 is the general chemical formula for poly(lactic-co-glycolic acid) (PLGA) 400. The poly(lactic-co-glycolic acid) (PLGA) polymer 400 is a biodegradable material that will ablate, wear away, and break down over time.

Figure 5:
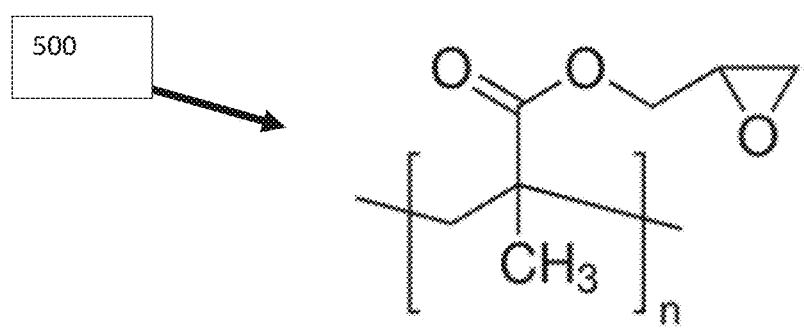
FIG. 5 is a chemical formula for polyglycidyl methacrylate (PGMA)

FIG. 5 is the general chemical formula for polyglycidyl methacrylate (PGMA). The polyglycidyl methacrylate (PGMA) polymer 500 is a biodegradable material that will ablate, wear away, and break down over time.

FIG. 6 is a chart showing the MERV levels for air filters as prescribed by ASHRAE. A MERV level of 13 or higher has been prescribed by the CDC for air filtration in office buildings, schools, residences and other occupied interior spaces.

The air filter may also have a means for detecting viral material that is impinged upon the filter. One such means for detecting the viral material is the utilization of single-stranded DNA couple to a microchip. When a material binds to the single-strand DNA, such as a single-strand RNA that is characteristic of the SARS-CoV-2, a difference in electrical charge may be determined by the microchip attached to the single-strand DNA. This electrical difference in the microchip will allow for the determination of the attachment of a specific RNA strand to a detector. As more and more RNA strands attached to the single-strand DNA, more of an indication may be seen from the microchip attached to the DNA single-strand material. This will generate a signal that will show the amount of single-stranded RNA attached to the single-strand DNA and thus identify both the viral load and the variant of the virus that is being detected. For instance, a single-stranded DNA with the sequence that matches the single stranded RNA of the Delta variant of the SARS-CoV-2 virus will bind with the viral RNA and cause a change in the electrical characteristics of the biosensor chip. This will show not only that the Delta variant is present but also the amount of Delta variant that is present.

The single-stranded DNA (ssDNA) detector may also be utilized to check the efficacy of the virucide filter. An ssDNA detector may be mounted downstream of a virucide infused filter such that the air passing through the virucide infused filter will subsequently come in contact with the ssDNA detector. The ssDNA detector will then detect any viral load that is coming through the virucide infused filter, indicating that the efficacy of the virucide infused filter has been lessened and report this lower virucide all activity through an electronic communication means.

The ssDNA detector may also be utilized as part of a system to indicate viral loads in a building or structure. The detectors may be placed in various areas of the building or structure and connected into a communications system, similar to a fire reporting communications system, such that viral infections in a building or structure, such as a hospital, may be registered and recorded and dealt with appropriately.

An array of biosensors may be utilized to detect multiple types of pathogens. For instance, biosensors set to detect the Alpha, Beta, and Delta variants of the SARS-CoV-2 virus would be utilized to detect not only the viral load in a specific area but the type of virus that is present.

In another aspect of the biosensor, the biosensor may be coated with a material that simulates a cell membrane, such as a lipid monolayer or bilayer or polysaccharide layer. The simulated cell membrane may also have simulated receptors for the target pathogens, such as SARS-CoV-2 viruses. The presence of this layer with simulate a cell membrane and fool the pathogen, such as a virus, to attaching and giving up its core nucleic acid for identification by the sensor.

Another aspect of this embodiment is the use of a specialized virucide, such as an enzyme like a RNA nuclease, to inactivate viral pathogens. The use of a Clustered Regularly Interspaced Short Palindromic Repeats (CRISPR)/CRISPR associated protein 13 (Cas13) may be utilized to cleave RNA nucleic acid sequences. In one manner, RNA nucleases cleave the phosphodiester bonds of nucleic acids in the RNA, inactivating a single stranded RNA virus (ssRNA) such as SARS-CoV-2. A phosphodiester bond is shown in FIG. 7. Cas13 targets RNA, not DNA. When it is activated by a ssRNA sequence that is complementary to its CRISPR-RNA (crRNA) spacer, the Cas13 releases nonspecific RNase activity and inactivates RNA in the Cas13 vicinity without regards to the RNA sequence. Thus, Cas13 coupled with crRNA forms a complex that may effectively inactivate ssRNA viruses such as SARS-CoV-2.

Each numerical value presented herein is contemplated to represent a minimum value or a maximum value in a range for a corresponding parameter. Accordingly, when added to the claims, the numerical value provides express support for claiming the range, which may lie above or below the numerical value, in accordance with the teachings herein. Every value between the minimum value and the maximum value within each numerical range presented herein, is contemplated and expressly supported herein, subject to the number of significant digits expressed in each particular range.

Having described herein illustrative embodiments of the present invention, persons of ordinary skill in the art will appreciate various other features and advantages of the invention apart from those specifically described above. It should therefore be understood that the foregoing is only illustrative of the principles of the invention, and that various modifications and additions, as well as all combinations and permutations of the various elements and components recited herein, can be made by those skilled in the art without departing from the spirit and scope of the invention. Accordingly, the appended claims shall not be limited by the particular features that have been shown and described but shall be construed also to cover any obvious modifications and equivalents thereof.

What is claimed is:

1. A device for inactivating a pathogen in an environment, the device comprising:
    a substrate;
    a coating comprising a polymer dried or cured onto the substrate, wherein the polymer comprises at least one of an ablative polymer and a sacrificial polymer comprising a material that wears away from at least one of a thermal interaction, a UV interaction, an energetic interaction, an oxidating interaction, and a hydrogenating interaction; and
    a pathogen inactivating material infused within the polymer, wherein, at a given time, a portion of the pathogen inactivating material is exposed to the environment, and wherein the device is configured to periodically or intermittently expose additional pathogen inactivating material to the environment.

2. The device of claim 1, wherein the substrate comprises a fiberglass material.

3. The device of claim 1, wherein the substrate comprises a paper material.

4. The device of claim 1, wherein the substrate comprises a woven material.

5. The device of claim 1, wherein the substrate comprises a non-woven material.

6. The device of claim 1, wherein the polymer comprises a copolymer.

7. The device of claim 1, wherein the pathogen inactivating material comprises at least one of a virucide and a biocide.

8. The device of claim 7, wherein the pathogen inactivating material comprises a virucide comprising at least one of: benzalkonium chloride, quaternary ammonium salt, and an enzyme that targets a virus.

9. The device of claim 1, wherein the pathogen inactivating material comes to the surface of the polymer through a passive transport mechanism.

10. The device of claim 9, wherein the passive transport mechanism comprises at least one of: surface energy, diffusion, and capillary action.

11. The device of claim 1, wherein the device comprises an air filter.

12. The device of claim 1, wherein the polymer comprises at least one of: polylactic acid, polycaprolactone, poly (lactic-co-glycolic acid), polyglycidyl methacrylate, gelatin, polysaccharides, cellulose acetate, ethyl cellulose, hydroxyethyl cellulose, and polyvinyl acetate copolymer.

13. The device of claim 12 where the pathogen inactivating material denatures the protein component of the pathogen, rendering it inactive.

14. The device of claim 12 where the pathogen inactivating material oxidizes the pathogen, rendering it inactive.

15. The device of claim 12 where the pathogen inactivating material utilizes an enzymatic process to inactivate the pathogen.

16. A method for inactivating a pathogen in an environment, the method comprising:

coating a substrate with a polymer infused with a pathogen inactivating material, wherein (i) the polymer comprises at least one of an ablative polymer and a sacrificial polymer comprising a material that wears away from at least one of a thermal interaction, a UV interaction, an energetic interaction, an oxidating interaction, and a hydrogenating interaction and (ii) the polymer infused with the pathogen inactivating material is configured to periodically or intermittently expose additional pathogen inactivating material to the environment; and drying or curing the coating onto the substrate.

17. The method of claim 16, wherein the polymer is a copolymer.

18. The method of claim 16, wherein the pathogen inactivating material comprises a virucide comprising at least one of: benzalkonium chloride, quaternary ammonium salt, and an enzyme that targets a virus.

* * * * *